United States Patent
Fadler et al.

(10) Patent No.: US 6,942,385 B2
(45) Date of Patent: Sep. 13, 2005

(54) METHOD AND DEVICE FOR POSITIONING A SLICE LEVEL OF AN X-RAY EXPOSURE

(75) Inventors: Franz Fadler, Hetzles (DE); Stefan Leidenberger, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 51 days.

(21) Appl. No.: 10/631,040

(22) Filed: Jul. 29, 2003

(65) Prior Publication Data

US 2004/0081281 A1 Apr. 29, 2004

(30) Foreign Application Priority Data

Jul. 29, 2002 (DE) .......................................... 102 34 465

(51) Int. Cl.⁷ .............................................. A61B 6/08
(52) U.S. Cl. ........................................ 378/205; 378/63
(58) Field of Search ............................. 378/21, 25, 26, 378/62, 63, 205, 206; 600/425, 429

(56) References Cited

U.S. PATENT DOCUMENTS

| | | | | |
|---|---|---|---|---|
| 3,916,192 A | * | 10/1975 | Schmitmann et al. | ......... 378/98 |
| 4,262,306 A | * | 4/1981 | Renner | ......................... 378/205 |
| 4,442,533 A | * | 4/1984 | Lescrenier | .................... 378/21 |
| 5,039,867 A | * | 8/1991 | Nishihara et al. | ........... 378/205 |
| 5,212,717 A | * | 5/1993 | Hada | .............................. 378/4 |
| 5,657,368 A | | 8/1997 | Röckseisen | |
| 5,933,472 A | | 8/1999 | Molz et al. | |
| 6,005,909 A | * | 12/1999 | Biermann et al. | ............. 378/21 |
| 6,502,984 B2 | * | 1/2003 | Ogura et al. | ................. 378/206 |

* cited by examiner

Primary Examiner—Edward J. Glick
Assistant Examiner—Chih-Cheng Glen Kao
(74) Attorney, Agent, or Firm—Schiff Hardin LLP

(57) ABSTRACT

In a method and device for positioning the level of a slice during the generation of a slice exposure of an examination subject with an x-ray examination device, a reference image of the exterior of the examination subject is recorded by a camera on a line of sight proceeding transverse to the direction of examination. The slice level of a subsequent slice exposure is determined using a slice level marking within the reference image.

16 Claims, 1 Drawing Sheet

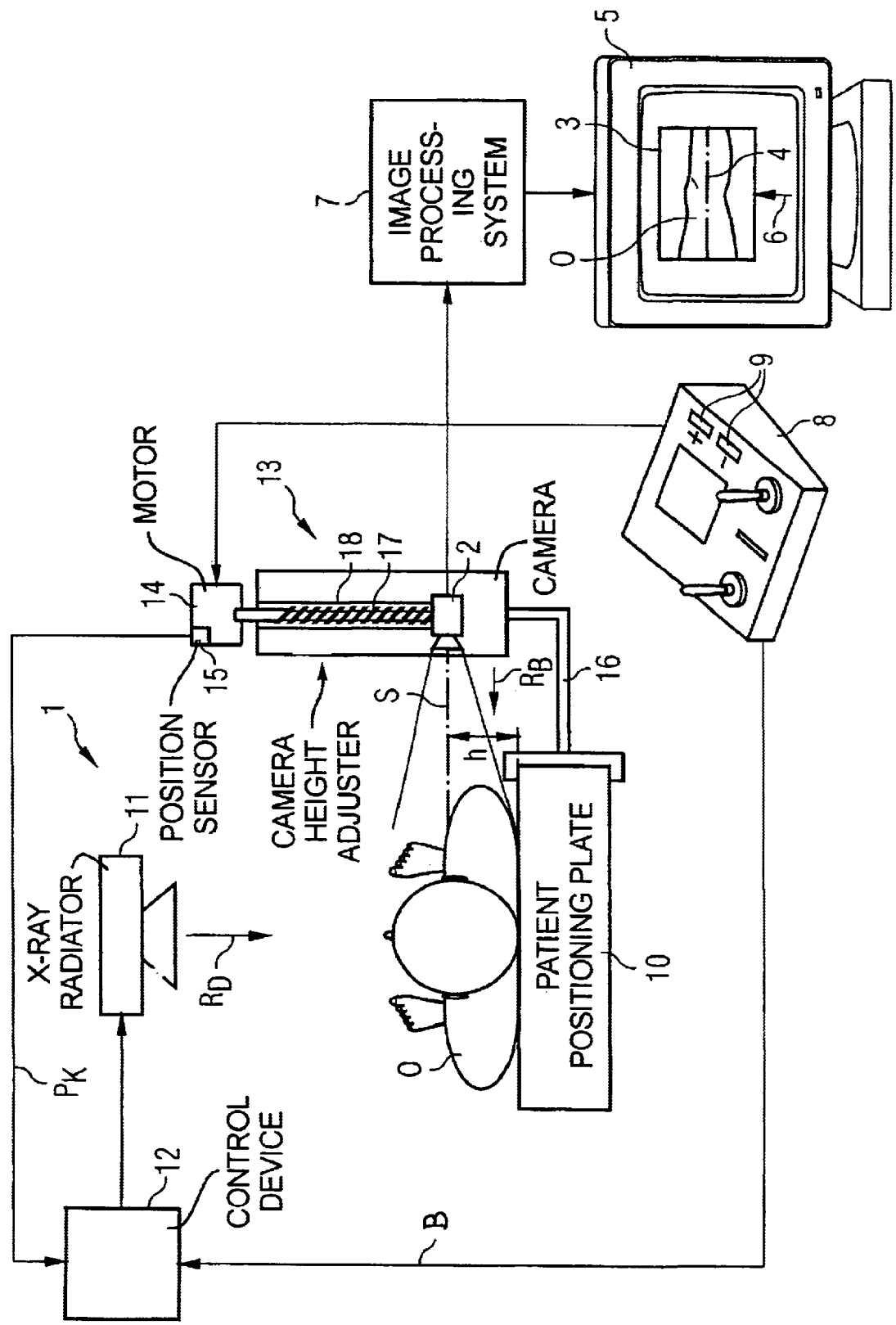

METHOD AND DEVICE FOR POSITIONING A SLICE LEVEL OF AN X-RAY EXPOSURE

BACKGROUND OF THE INVENTION

1. Field of the Invention

The present invention concerns a method for positioning the level of a slice in the generation of a slice acquisition of an examination subject with an x-ray examination device. The invention also concerns a corresponding slice-level positioning device for positioning the level of a slice in the implementation of a slice acquisition of an examination subject with an x-ray examination device, as well as an x-ray examination device with such a device for positioning the level of a slice.

2. Description of the Prior Art

With appropriately equipped x-ray examination devices (referred to as "sliceable") such as, for example, above-table examination devices, Bucky tables, or similar diagnostic procedure stations, it is possible to generate a slice exposure from an examination subject (for example, from a patient) in which, for the most part, only the structures located in a defined slice plane are clearly recognizable. In addition, the various parameters of the x-ray examination device are set such that all regions before and after the desired slice plane are blurred, i.e. they are recorded fuzzy, and only the structures in the slice layer are clearly reproduced. Selective information thus can be obtained about very definite organs or bone structures of a patient, for example the patella or the spinal canal. The slice level is the position of the desired slice plane in the radiation path between the x-ray radiator and the x-ray detector (which, in the cited diagnostic procedure stations, is normally located beneath the patient) and must be positioned as exactly as possible before the exposure by the operating personnel. For exact positioning of the slice level, and thus for exact orientation of the images of definite body slices of the patient detected with the help of slice exposure, slice-level indicators are generally used that project light crosses, laser markings, etc. onto the patient as an aid, and thereby visibly mark the actual slice level set on the device on the patient for the operator. In addition, a corresponding projection device is mounted on the x-ray examination device, for example on the patient positioning plate. Different exemplary embodiments of such slice level light beam localizers are described in German Patent 197 04 703, for example. Laser marking devices are also configured for other purposes such as, for example according to German OS 44 21 315, aid for a tumor position marking on the body of a patient before exchanging a computed tomography assembly on a therapy device.

A disadvantage of the known slice level indicators and devices for the positioning of the level of a slice, is that the operator must stay by the patient in order to exactly position the slice level with the aid of the slice level indicators. During the exposure, the operator must then leave the x-ray room for reasons of radiation protection. If a further slice recording is to be generated at another slice level, the operator must once again return to the patient in order to undertake a new positioning.

SUMMARY OF THE INVENTION

An object of the present invention to provide an alternative to known techniques and devices for positioning the slice level of an x-ray exposure, which enables substantially more convenient and faster positioning of the slice level.

This object is achieved in accordance with the invention in a method and device wherein a reference image of the exterior of the examination subject is recorded by a camera from a line of sight proceeding transverse, preferably at right angle, to the direction of the x-ray examination. The slice level of a subsequent slice exposure is then determined using a slice level marking within the reference image.

The camera can be directly integrated into a device component of the x-ray examination device, for example the x-ray tube support arm. It is also possible for the camera to be mounted, preferably detachably, to a device component, for example a patient orientation plate, be means of an attachment device. This has the advantage that existing x-ray examination devices can be retrofitted with an inventive device for the positioning of the level of a slice.

The positioning device has an indicating unit for the indication of the reference image, and a marking unit for marking a desired slice level within this reference image. The device for the positioning of the level of a slice also includes a processor for determining the slice level using the slice level marking in the reference image.

The slice level determined in this manner is then transmitted, for example, to a control device of the x-ray examination device, which controls the x-ray examination device, i.e. implements the exposure parameters such as, for example, the distance of the x-ray radiator from the detector, etc., such that the acquired slice lies in the inventively determined slice level.

With the inventive method and device for positioning the level of a slice, it is possible that the operator of the x-ray examination device can implement the positioning of the slice level directly from a control console or the like located outside of the x-ray room, without entering the x-ray room. The positioning of the slice level consequently can ensue more comfortably and more quickly for the operator, which decreases the total examination time and thus also has advantages for the patient. Furthermore, there is the advantage that the patient can be monitored by the operating, personnel via the camera during the examination.

As used herein an x-ray examination device, is any imaging device with an x-ray source that does not rotate around the examination subject during the exposure, thus in particular a radioscopic or fluoroscopic device, but also a conventional imaging station (radiography device). Thus, an image amplification system with TV camera or CCD detector, or even a common film/foil system (in a cassette), can be available as a detector. As a result, a CT device is not considered as an x-ray examination device herein.

Various possibilities exist for determining the slice level using the slice level. markings within the reference image.

In a preferred, simple version, the slice level is determined using position data of the slice level marking within the reference image, as well as using the position data of the camera with respect to the x-ray examination device, i.e. for example relative to the surface of the patient positioning plate. In this version, the device for the positioning of the level of a slice includes an appropriate camera position measurement detector to identify the position data of the camera. Furthermore, appropriate means (such as, for example, a calculating device) must be present in order to determine the slice level using the position data of the slice level marking within the reference image and using the position data of the camera, i.e., the slice level must be converted between the coordinate systems.

In an alternative method and device, the reference image is subjected to image processing to identify fixed points within the reference image, for example in the patient positioning plate, the position data of which are known with reference to the x-ray examination device. The slice level can then be determined with a calculating device, using the position data of the slice level marking relative to the recognized fixed points within the reference image, as well as using the position data of the fixed points in the room, i.e. with reference to the x-ray examination device. This method and device have the advantage that the camera does not require any position measurement device, but a more complex image-processing device is required, for example appropriately powerful image processing software.

There are various possibilities, as necessary, for the application of the markings within the reference image.

In a simple, preferred method, the slice level marking is fixed within the reference image detected by the camera. The camera is controlled for slice level positioning such that the reference image detected by the camera is varied, i.e., the image slice is moved, for example, by displacing the camera and/or tilting the camera, until the marking within the image, slice lies on the corresponding position of the examination subject. This fixed slice level marking can ensue via the camera itself and/or an appropriate indicator device,. for example, such that a marking is arranged on the objective of the camera, which is transmitted to the indicator device as an image, or such that the indicator device inserts the marking at a fixed position in an image processing system. The advantage of such a slice level marking arranged within the detected reference image is that the camera position data can be directly used for adjustment of the slice level without significant conversion, since only the offset between the measurement points at which the camera position is determined and the position of the defined slice level marking must be considered. If, for example, the slice level marking is always located within the middle of the image slice to be obtained, and the measurement point of the camera position corresponds as needed to the middle of the image slice detected by the camera, and the camera position data can be directly used as slice level position data, without conversion, and be transmitted to a control device of the x-ray examination device.

To adjust the detected reference image, the camera preferably is moved parallel to the direction of examination, i.e. it is adjusted in height relative to the patient positioning plate. The device for the positioning of the height of a slice additionally includes an adjustment device to move the camera. Such a camera level adjustment is realizable in a comparatively simple manner. Furthermore, it is also possible to arrange the camera such that it can be moved or pivoted in other directions. The adjustment device preferably is operable via a remote control device.

In an alternative exemplary embodiment, the device for the positioning the level of a slice includes appropriate means, for example a graphical user interface and input device, in order to arbitrarily set the slice level marking within the reference image detected by the camera. Since the slice level marking is not set with reference to the camera position, the position data of the slice level marking within the reference image must be converted in this version into position data of the slice level in physical space for each of the position determination movements described above.

In a preferred exemplary embodiment, suitable recording parameters are stored in a memory of the device for positioning the level of a slice for various image types, for example for a spinal column image or a meniscus image. Such databanks are known and are referred to as "organ program." Such organ programs operate so that the operator must enter only the image type, and possibly patient-specific parameters such as, for example, gender, age, weight, knee thickness, etc., and the appropriate imaging parameters are then automatically configured in the x-ray examination device. In the execution of the inventive method in connection with an organ program, at least one parameter of the examination subject, for example the knee thickness, is determined by image processing of the reference image during the slice level positioning. An optimal slice level can then be determined automatically for one of the imaging types chosen by the operator on the basis of the stored imaging parameters pertaining thereto from the organ program and the determined parameter of the examination subject. This slice level can then be indicated as a recommendation in the reference image by a marking. The operator then can either approve the indicated slice level indicated by the automatic marking via an appropriate operator interface or, if necessary, can change it if the operator disagrees with the suggestion.

With such an automatic method, the positioning of the optimal slice level for a particular image type becomes even simpler for the operator. In addition, the workflow is optimized, since the operator no longer has to measure the parameters of the examination subject himself and determine the correct slice level using tables or by estimation.

DESCRIPTION OF THE DRAWINGS

The single FIGURE is a schematic illustration of an x-ray examination device with an inventive device for the positioning of the level of a slice.

DESCRIPTION OF THE PREFERRED EMBODIMENTS

The x-ray examination device in the exemplary embodiment is as an x-ray radioscopy device.

As is shown in the FIGURE, the x-ray examination device 1 has a patient positioning plate 10, over which is located an x-ray radiator 11. An x-ray detector (not shown) such as an x-ray image intensifier together with a TV camera, is located within or underneath the patient positioning plate (or table) 10. The examination subject O (the patient) is positioned on the patient positioning plate 10 such that the subject is located in the path of the radiation between the x-ray radiator 11 and the detector.

The parameters necessary for the exposure are set in the x-ray radiator 11 and, if necessary, also in the detector with a controller 12 which includes the voltage generator and further components such as adjustment devices, etc. This means, for example, that the distance of the x-ray radiator 11 from the surface of the patient positioning plate 10 is set, the dosage fixed, etc.

A slice image of a structure in the examination subject O located in a precisely determined slice plane S ensues dependent upon the set parameters. In addition, the position data of the slice plane S, i.e. the slice level h above the surface of the patient positioning plate 10, must be supplied by the controller 12.

The adjustment of the slice level h is provided by a device for positioning of the level of a slice having a digital camera 2 that produces a reference image of the exterior of the examination subject O on a line of sight RB proceeding at a right angle to the direction of examination $R_D$. The image recorded by the camera 2 is processed in an image processing system 7 and displayed on a monitor 5, which can be a monitor belonging to an image processing station of the x-ray examination device 1. A specific screen region, for example a special screen window 6 provided for this in a more complex program, displays the reference image 3 recorded by the camera in a picture-in-picture format.

A slice level marking 4 is indicated within the reference image 3 on the monitor 5 which, for example, is superimposed by the image processing system 7 onto the reference image originally recorded by camera 2. The exemplary embodiment in the FIGURE shows a slice level marking 4 (fixed with respect to the reference image 3) which is always shown as a line in the middle of the reference image 3.

The camera 2 is adjustably mounted by a camera height adjuster 13 next to the patient positioning plate 10, such that the camera height can be adjusted (meaning parallel to the direction of examination RD). The camera height adjuster 13 has a linear guide 18 for the camera 2, and the camera 2 is connected by a spindle 17 to a motor 14. Given rotation of the shaft of the motor 14, the camera 2 is adjusted up or down along the linear guide 18. The camera height adjuster 13 is detachably mounted by a carrier arm 16 to the patient positioning plate 10, for example by clamping, such that the camera 2 is adjustable over the entire applicable height range.

The motor 14 is controllable by a remote control console 8. This control console 8 is, like the monitor 5, located outside of an x-ray room inside a control room in which the operator stays during an exposure. The operator can then control the motor 14 using corresponding slice level adjustment keys on the control console 8, and thus moves the camera 2 such that its height is adjusted with reference to the patient positioning plate 10. The image slice thereby recorded by the camera 2 (i.e. the reference image 3) is shifted, whereby the slice level marking 4 is also automatically shifted relative to the examination subject O).

The slice level marking 4 within the reference image 3 (which shows the examination subject O) or the examined part of the examination subject O (here, as an example, the knee of the patient) then indicates the slice level h of the slice exposure (image) that will be obtained.

A position sensor 15 is located in the motor 14 that measures the position of the motor 14 and thus the level position of the camera 2. This position data PK of the camera 2 is directly transmitted to the controller 2. Using the transmitted camera position data PK, the likewise known position of the patient positioning plate 10, as well as, if necessary, the known position of the slice level marking 4 within the reference image 3, the slice level h of the recorded slice is clearly defined for the controller 12 in reference to the patient positioning plate 10. After fixing the desired slice level h with the aid of the slice level adjustment keys 9 and the reference image 3 with the slice level marking 4 displayed on the monitor 5, the operator can then send a confirmation signal B to the controller 12. After receiving the confirmation signal B, the controller 12 automatically accepts the ongoing camera position data Pk received from the position sensor 15 to determine the slice level h. The controller 12 can thus automatically appropriately set the required parameters of the x-ray examination device 1 in order to generate a slice recording in the desired slice plane S which is marked in the image 3.

The exemplary embodiment according to the FIGURE is a relatively simple, uncomplicated, and thus economic assembly. Since the camera 2 or the camera height adjuster 13 is attached by a carrier arm 16 to the patient positioning plate 10, the system can operate independently of the position of the patient positioning plate 10 (i.e. also during a pivoting of the patient positioning plate 10) without a rearrangement of the device for positioning the level of a slice. A retrofitting of existing x-ray examination devices is possible at any time due to the detachable mounting (for example, a clamp) of the camera 2, together with the height adjuster 13, to the patient positioning plate 10.

In addition to the above-described exemplary embodiment, other different possible variations for realizing an inventive device for the positioning of the level of a slice are apparent. For example, the remote control console 8 and the monitor 5, as well as the image processing system 7, can be completely integrated using appropriate software into an existing control device of the x-ray examination device, such as a PC. For example, the customary toggle-keys of a PC keyboard, or a joystick, a mouse or the like, can be used as slice level adjustment keys.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for positioning a level of a slice of an X-ray exposure to be generated by irradiating a subject in an examination direction, said method comprising the steps of:
    obtaining a reference image of an exterior of a subject with a camera along a line of sight transverse to said examination direction;
    indicating a selected slice level with a marking in said reference image; and
    using said marking in said reference image for automatically electronically setting operating parameters of an X-ray examination device when irradiating the subject with X-rays with said X-ray examination device to generate an unblurred image of substantially only said slice level of said subject.

2. A method as claimed in claim 1 wherein said marking has marking position data within said reference image associated therewith and wherein said camera has camera position data with reference to said X-ray examination device associated therewith, and using said marking position data and said camera position data to set said slice level.

3. A method as claimed in claim 2 comprising subjecting said reference image to image processing to detect fixed points therein having position data associated therewith that are known with reference to the X-ray examination device, and setting said slice level using said marking position data relative to said fixed points in said reference image and using the position data of the fixed points with reference to the X-ray examination device.

4. A method as claimed in claim 3 comprising fixing said marking within said reference image and moving said camera to vary said reference image.

5. A method as claimed in claim 4 comprising moving said camera parallel to said examination direction to vary said reference image.

6. A method as claimed in claim 1 comprising manually designating the slice level marking in said reference image.

7. A method as claimed in claim 1 comprising the steps of:
    storing imaging parameters in a memory for a plurality of different types of images obtainable using said X-ray examination device;
    subjecting said reference image to image processing to determine a subject parameter of said subject;
    setting a slice level for one of the types of images, selected by an operator of the X-ray examination device, using said subject parameter and the imaging parameters stored in the memory for the selected type of image;

visually displaying said reference image with said marking therein corresponding to the slice level that has been set; and allowing an operator of the X-ray examination device to approve the slice level designated by the marking in the displayed reference image and to fix the slice level for irradiating the subject with X-rays with said X-ray examination device to obtain the selected type of image.

8. A slice level positioning device for positioning a level of a slice of an X-ray exposure to be generated by irradiating a subject in an examination direction, comprising:

a camera for obtaining a reference image of an exterior of a subject along a line of sight transverse to said examination direction;

an indication unit indicating a selected slice level with a marking in said reference image; and a processor using said marking in said reference image for setting operating parameters of an X-ray examination device when irradiating the subject with X-rays with said X-ray examination device to generate an unblurred image of substantially only said slice level of said subject.

9. A slice level positioning device as claimed in claim 8 wherein said marking has marking position data within said reference image associated therewith and wherein said camera has camera position data with reference to said X-ray examination device associated therewith, and wherein said processor sets said slice level using said marking position data and said camera position data.

10. A slice level positioning device as claimed in claim 9 comprising an image processor for subjecting said reference image to image processing to detect fixed points therein having position data associated therewith that are known with reference to the X-ray examination device, and wherein said processor sets said slice level using said marking position data relative to said fixed points in said reference image and using the position data of the fixed points with reference to the X-ray examination device.

11. A slice level positioning device as claimed in claim 10 wherein said indication unit fixes said marking within said reference image, and comprising a camera height positioner for moving said camera to vary said reference image.

12. A slice level positioning device as claimed in claim 11 wherein said camera height positioner moves said camera parallel to said examination direction to vary said reference image.

13. A slice level positioning device as claimed in claim 11 wherein said camera height positioner is remotely controllable.

14. A slice level positioning device as claimed in claim 8 comprising an input unit allowing manual designation of the slice level marking in said reference image.

15. A slice level positioning device as claimed in claim 8 comprising:

a memory for storing imaging parameters for a plurality of different types of images obtainable using said X-ray examination device;

an image processor for subjecting said reference image to image processing to determine a subject parameter of the examination subject;

said processor for setting a slice level setting operating parameters for a selected one of the types of images using said subject parameter and the imaging parameters stored in the memory for the selected type of image;

a display for visually displaying said reference image with said marking therein corresponding to the slice level that has been set; and an input unit allowing an operator of the X-ray examination device to approve the slice level designated by the marking in the displayed reference image and to fix the slice level for irradiating the subject with X-rays with said X-ray examination device to obtain the selected type of image.

16. An X-ray examination device allowing positioning of a level of a slice of an X-ray exposure comprising:

an X-ray arrangement for irradiating a subject in an examination direction to produce an X-ray exposure;

a camera for obtaining a reference image of an exterior of the subject along a line of sight transverse to said examination direction;

an indication unit for indicating a selected slice level with a marking in said reference image; and a processor using said marking in said reference image for setting operating parameters of said X-ray arrangement when irradiating the subject with X-rays with the X-ray arrangement to generate an unblurred image of substantially only said slice level of said subject.

* * * * *